United States Patent [19]
Prestel

[11] Patent Number: 5,968,074
[45] Date of Patent: Oct. 19, 1999

[54] SURGICAL INSTRUMENT

[75] Inventor: Stephan Prestel, Rheinstetten-Mörsch, Germany

[73] Assignee: Richard Wolf GmbH, Knittlingen, Germany

[21] Appl. No.: 09/118,952

[22] Filed: Jul. 17, 1998

[30] Foreign Application Priority Data

Jul. 24, 1997 [DE] Germany ............... 297 13 150 U

[51] Int. Cl.[6] ............... A61B 17/28; A61B 17/42; A61B 17/44
[52] U.S. Cl. ............... 606/205; 606/207
[58] Field of Search ............... 606/205, 207, 606/208, 206

[56] References Cited

U.S. PATENT DOCUMENTS

| | | | |
|---|---|---|---|
| 4,712,545 | 12/1987 | Honkanen | 128/305 |
| 4,887,612 | 12/1989 | Esser et al. | 128/751 |
| 5,456,695 | 10/1995 | Herve Dallemagne | 606/207 |
| 5,478,351 | 12/1995 | Meade et al. | 606/205 |

*Primary Examiner*—Michael Buiz
*Assistant Examiner*—Uy Q. Bui
*Attorney, Agent, or Firm*—Cohen, Pontani, Lieberman & Pavane

[57] ABSTRACT

A surgical instrument having at least two distal jaw parts each having a proximal part, an instrument holder for enabling a user to hold the surgical instrument, a pull-push rod connected to the jaw parts for pivotably moving the jaw parts such that the jaw parts are movable commonly and in opposite directions from one another, and a sliding block guide for guiding movement of the push-pull rod consisting of a circular arc-shaped groove foamed in the proximal part of each the jaw part. Each circular groove in each respective jaw part is displaced by 180° from another circular groove in another jaw part. Each circular groove defining a virtual circle. At least two circular arc-shaped groove blocks are disposed on the instrument holder. Each circular groove block being configured to slidably engage a corresponding circular groove, such that a center of each virtual circle is defined about each groove block and at least two linkage arms for enabling the pull-push rod to manipulate the jaw parts, each having a first end and a second end. The first end of each linkage arm being connected to the push-pull rod, and the second end of each linkage rod being connected to the proximal part of the corresponding jaw part at a linkage point positioned at a predetermined distance from the virtual circle defined by the circular groove of said corresponding jaw part.

9 Claims, 5 Drawing Sheets

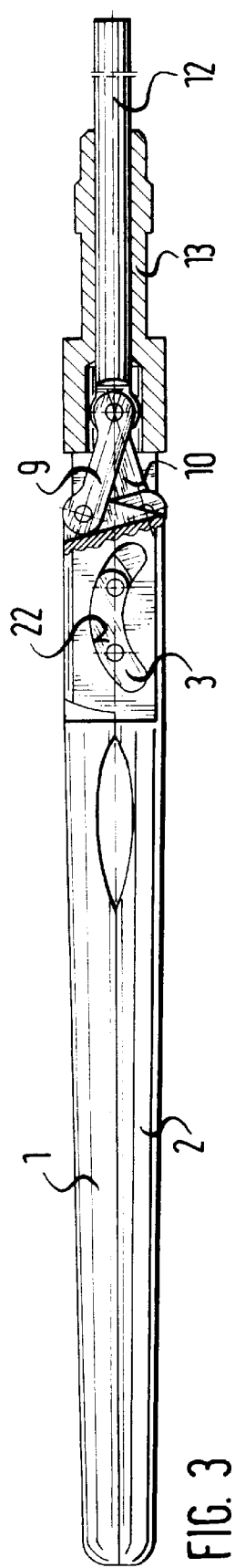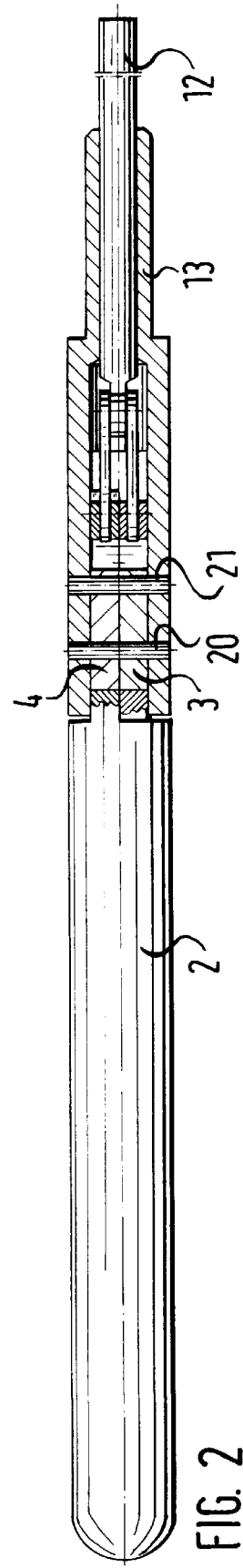

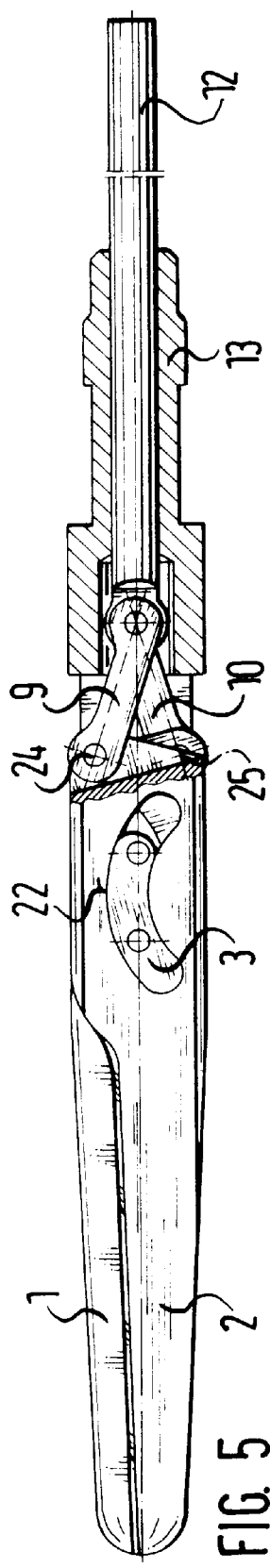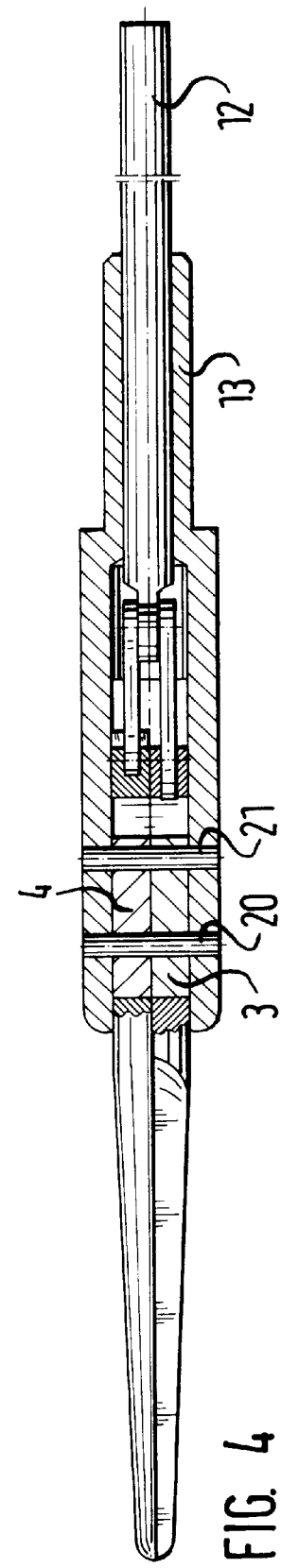
FIG. 5
FIG. 4

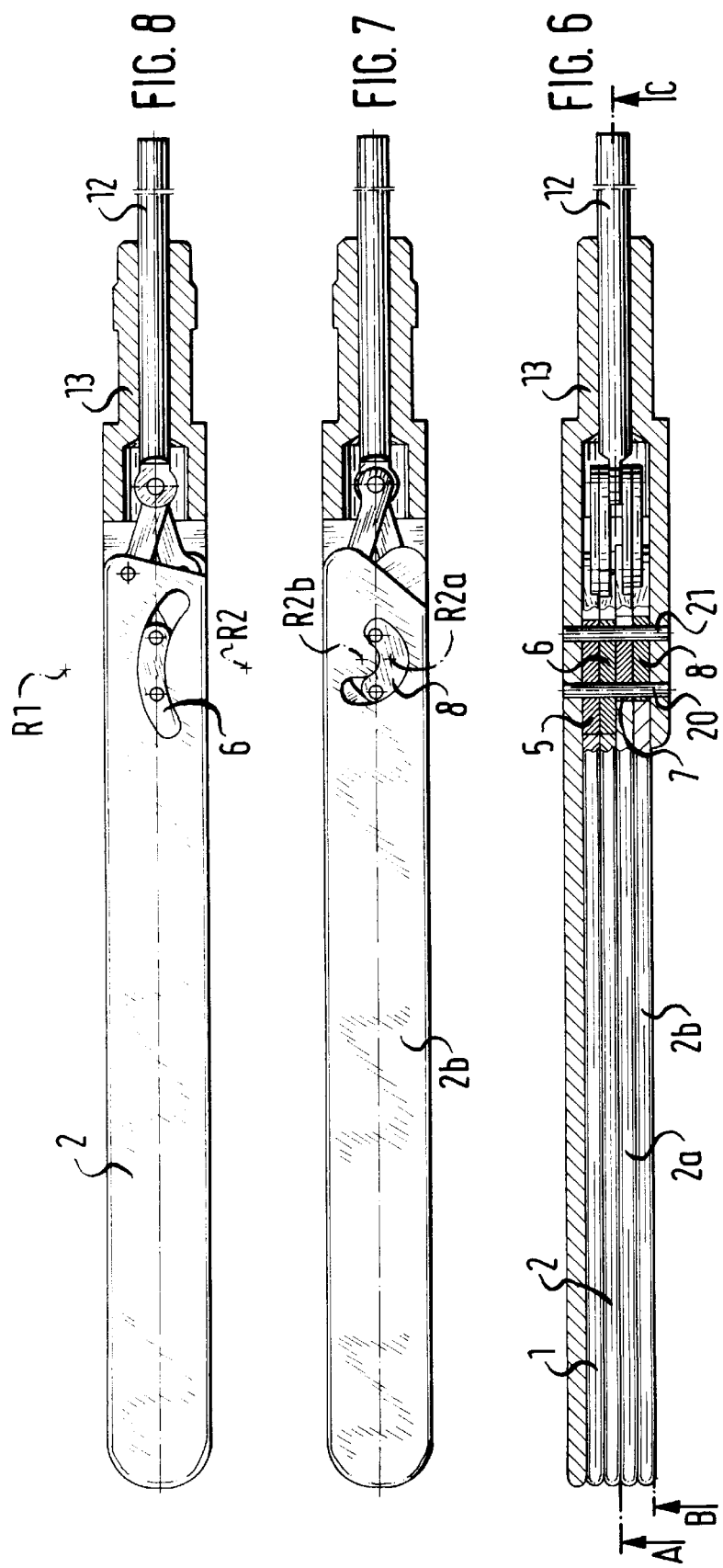

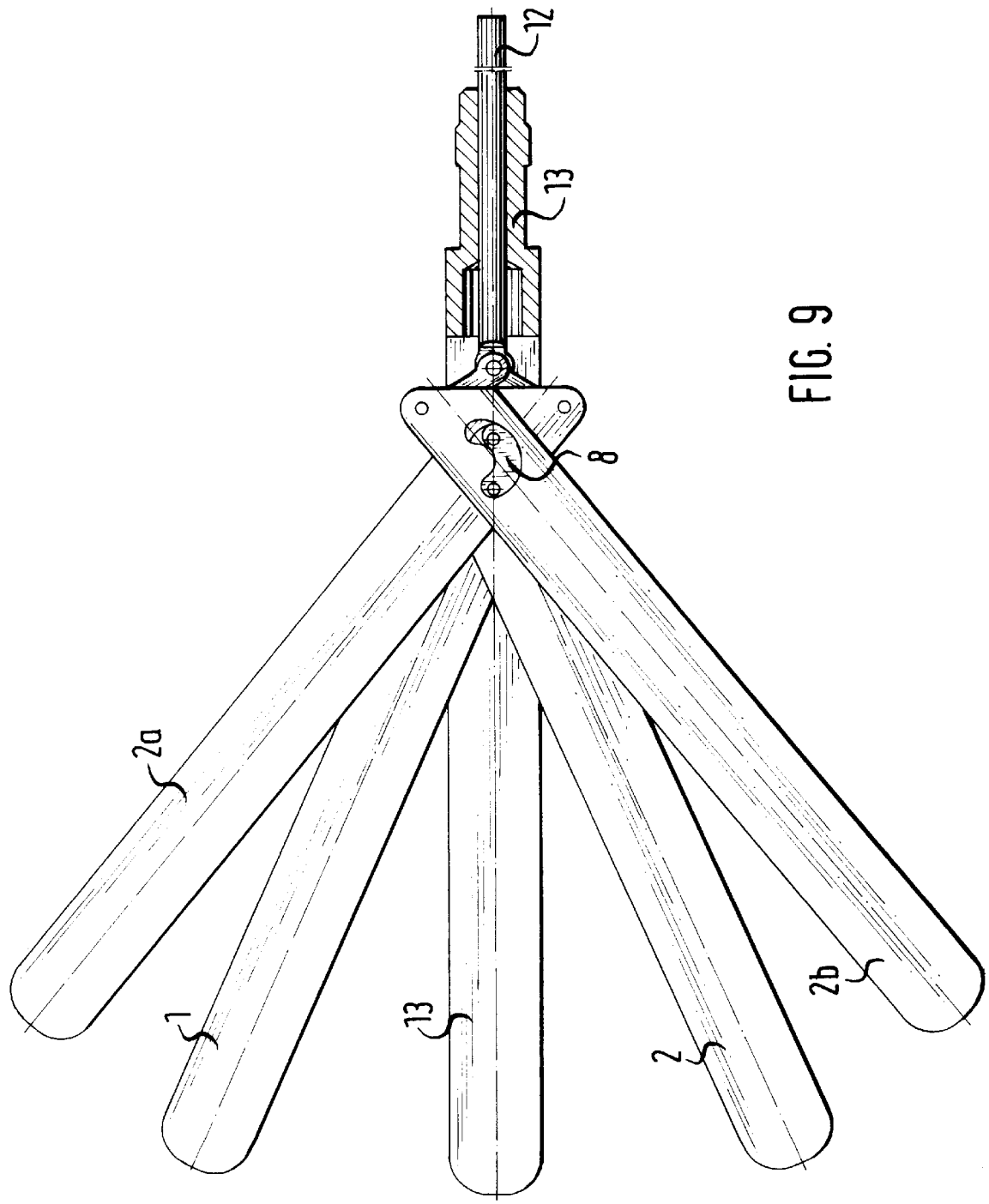

SURGICAL INSTRUMENT

BACKGROUND OF THE INVENTION

The invention relates to a surgical instrument with at least two distal jaw parts actuatable commonly and in opposite directions in a pivotingly movable manner by a pull-push rod, whose movement is guided by a sliding block guide consisting of a groove arranged in the jaw parts and a groove block engaging into the groove, wherein each jaw part on the proximal side comprises a circular arc shaped groove which in jaw parts neighboring one another are each arranged displaced by 180°.

Such a surgical instrument is known for example from the U.S. Pat. No. 4,887,612. With this instrument the jaw parts are each pivotable commonly and in opposite directions about a journal bearing, as a point of rotation, lying on the longitudinal axis of the instrument. Since the section line of the force exerted by the pull-push rod goes through this journal bearing serving as a pivoting bearing of the two jaw parts and also through the groove block common to both annular grooves, no reduction in force of the movement of the jaw parts with the pull-push rod is possible.

The U.S. Pat. No. 4,712,545 describes a surgical instrument with which for the pivoting movement of a single pivotable jaw part a virtual point of rotation lying outside the shank is formed by a sliding block guide so that here a reduction in force on moving the movable jaw part is achieved. However with this solution known from this US patent only instruments with a single movable jaw part may be realised. This is due to the fact that the grooves are incorporated in the inner flanks of the outer jaw part and the outer flanks of the inner jaw part. Furthermore the grooves and guides can only be manufactured with difficulty which increases the cost of manufacture.

BRIEF SUMMARY OF THE INVENTION

It is the object of the invention, inasmuch as to provide an improved instrument of the known type with which without much use of force on the grip of the forceps, i.e. on the pull or push rod, a delicate and continuous pivoting movement and when required, a movement of the jaw parts with high closing forces can be achieved and at the same time a non-tiring operation is made possible. Furthermore a parallel closing of the jaw parts for gripping or manipulating is to be made possible.

According to the invention this object is achieved with an instrument of the previously mentioned type such that each circular arc shaped groove block engaging in the respective groove is fixed on an instrument holder and by way of this for each jaw part a point of rotation in the virtual center of the circle defined by the circular arc shaped groove is formed and that the pull-push rod engages on the jaw parts by way of linkage arms linkedly connected to the pull-push rod and the jaw parts, whose linkage points at the proximal side end of the jaw parts lie in each case at a defined distance from the circles defined by the associated circular arc shaped grooves.

With the instrument according to the invention in comparison to the known instruments an approximately double as high a force is achieved on the jaw parts by improved lever ratios and a parallel closing of the jaw parts. In this way the force effort at the forceps grip is reduced or the force exerted by the jaw parts given the same effort of force is increased with respect to the known instruments. For the user there therefore results a lower strain.

Advantageously the circular arc shaped groove blocks are commonly fixed by two through-pins on the instrument holder. It is further advantageous when the arc length of the groove blocks distally of the mentioned pins is longer than the arc length of the groove blocks proximally of the pins. In this manner a larger guiding surface can be achieved.

With a particularly advantageous embodiment form of the invention the width of the groove block is smaller than the width of the jaw part at the location of the grooves. With this it is achieved that pressure from the retaining part fork can be exerted on the jaw part from the side, this being particularly important for scissors.

For manipulators also more than two jaw parts may be contained in the instrument according to the invention, which either are actuatable commonly via a corresponding number of linkage arms with a single pull rod or in each case in pairs by several pull rods.

Further with such an embodiment form of the instrument as a manipulator, several radii of curvature of the grooves may cause varying movements, i.e. particularly pivoting angles.

Furthermore a further formation is possible in which when the instrument according to the invention is formed as a manipulator, with the pair of jaw parts which in each case are commonly actuatable, the distance of the linkage points of the linkage arms to the associated grooves are selected differently.

BRIEF DESCRIPTION OF THE DRAWINGS

The invention is hereinafter described in more detail by way of embodiment examples shown in the drawings. There are shown.

DETAILED DESCRIPTION OF THE INVENTION

Figure 1:
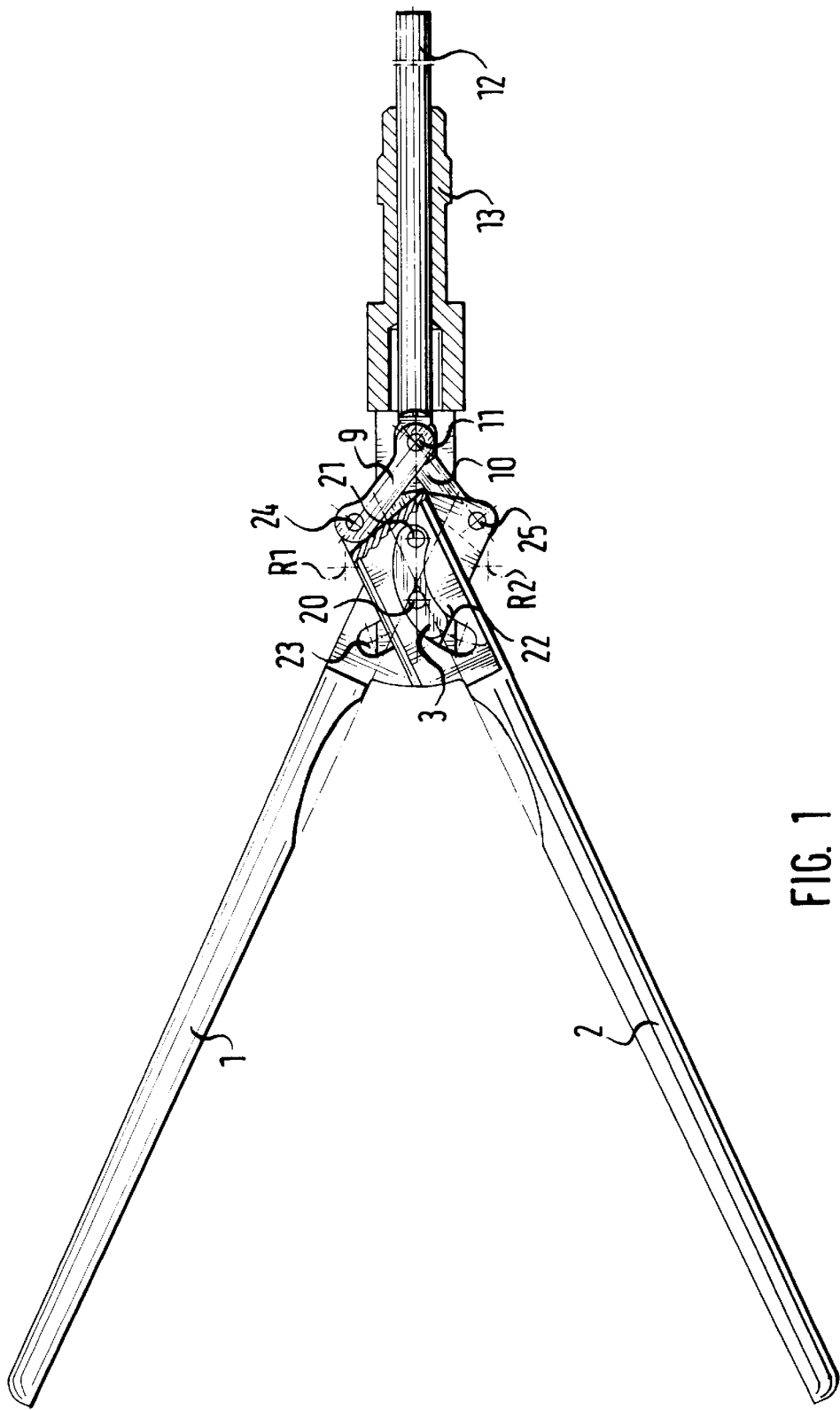
FIG. 1 schematically and at the proximal end partly sectioned, a distal part of an instrument formed as a clamp with two movable, opened jaw parts in a lateral view, FIG. 2 the same clamp as FIG. 1, partly sectioned, but in a lateral view turned around by 90°, FIG. 3 the instrument shown in FIG. 1 in the folded together condition of the jaw parts, FIG. 4 partly sectioned, an instrument formed as a scissors, from above, FIG. 5 the scissors represented in FIG. 4 from one side and partly in section and FIGS. 6 to 9 an embodiment form of the instrument according to the invention as a manipulator, specifically in FIG. 6 with a closed jaw part from above and partly sectioned, in FIG. 7 as a sectioned representation along the section line B–C in FIG. 6, in FIG. 8 as a sectioned representation along the section line A–C in FIG. 6 and in FIG. 9 from the side in the folded out condition of the individual jaw or branch parts.

With the instrument represented in FIG. 1 in one embodiment form as a clamp or forceps the two jaw parts 1, 2 in each case comprise a circular arc shaped groove 22, 23. These two grooves 22, 23 are in each case arranged displaced to one another by 180°. The shape of the grooves 22, 23, i.e. their radii of curvature plays a role for the pivoting angle of the two jaw parts 1, 2 and influences also the force to be exerted by the pull-push rod of the instrument for the movement of the jaw parts 1, 2. The smaller the radius of curvature of the grooves 22, 23 and of the groove blocks 3, 4 sitting in them and guiding the jaw parts, the larger is the maximum pivoting angle of the jaw parts 1, 2. The length of the grooves 22, 23 in relationship to the length of the groove blocks 3, 4 influences also the maximum pivoting angle of the two jaw parts 1, 2.

FIG. 1 shows that the groove blocks 3, 4 in relation to the pins 20, 21 are longer on the distal side than at their proximal ends, in order thus to achieve a larger guiding surface. Outside of the circle defined by the circular arc shaped grooves pivoting journals 24, 25 are provided, on which there are linked linkage or pivoting arms 9, 10, which for their part are connected to the pull-push rod 12 via a pivoting journal 11.

According to the laws of lever mechanics the force to be applied by the pull-push rod 12 and thus also the force to be applied on the forceps grip which is not shown by way of user depends on the distance of the pivoting journals 24, 25 from the virtual point of rotation, i.e. the center point of the circular arc defined by the grooves 22, 23.

The virtual point of rotation of the jaw part I lying outside the instrument shank or holder 13 is indicated at R1 and the virtual point of rotation of the jaw part 2 likewise lying outside the holder is indicated at R2. By way of this position of the virtual points of rotation R1, R2 the force ratios on pivoting movement of the two movable jaw parts 1, 2 effected with the pull-push rod is improved. The groove blocks 3, 4 are fixed to an instrument holder 13 to be seen in section by way of two pins 20, 21 commonly passing through them.

In contrast to the solution for example known from the previously mentioned U.S. Pat. No. 4,878,612 with the common pivoting point of the two jaw parts lying on the instrument axis, the force required for moving the jaw parts of the embodiment form of FIG. 1 is almost halved. This also means that the force acting through the jaw parts 1, 2 of the clamp or forceps shown in FIG. 1 onto the tissue, with the same force on the pull-push rod with regards to the solution represented in U.S. Pat. No. 4,878,612, becomes almost double as high. Furthermore with this instrument a parallel movability of the jaw parts 1, 2 in an almost closed condition of these is possible.

The sectioned view in FIG. 2 which shows the instrument shown in FIG. 1 from above, this being in a condition in which the jaw parts 1, 2 are folded together (the pull-push rod 12 is pulled back within the instrument holder 13), clearly shows the pins 20, 21 which are fixed on the instrument holder 13 and which commonly pass through the groove blocks 3 and 4 thus fixing these on the instrument holder 13.

FIG. 3 shows the same condition of the clamp as FIG. 2, but from one side. The pull-push rod is pulled back within the instrument holder 13. The groove blocks 3, 4 in each case lie at the distal ends of the grooves 22, 23 in the jaw parts 1, 2.

The FIGS. 4 and 5 show a surgical instrument formed as a scissors in each case in the same views as the clamp according to the invention described previously by way of FIGS. 1 and 2. In FIG. 4 the scissors can be recognized from above with closed scissor blades 1a, 2a and in FIG. 5 in the same condition from one side.

The instrument, as has been previously described and shown in the FIGS. 1 to 5 comprises two individual jaw parts 1, 2 pivotingly movable together in opposite directions, and the same length and equally curved groove blocks 3, 4 and grooves 22, 23 guided thereon. Furthermore the linkage points of the linkage arms 9, 10 lie on the jaw parts symmetrical to the longtudinal axis of the instrument and thus have in each case the same distance from the circle defined by the grooves and the groove blocks.

The FIGS. 6 to 9 show a further embodiment form of the instrument according to the invention formed as a manipulator. In the FIGS. 6 to 8 the manipulator is shown with closed jaw and branch parts 1, 2, 1a, 2b and in FIG. 9 with opened jaw or branch parts. FIG. 6 shows that in the respective grooves of the four jaw or branch parts 1, 2, 1a, 2b there engage four groove blocks 5, 6, 7, 8 which are commonly fixed to the instrument holder 13 by two pins 20, 21.

The sectional view along the section line B–C shown in FIG. 7 shows the manipulator from one side and thus only the one jaw or branch part 2b and the groove provided in this as well as the groove block 8 engaging into this groove. The sectioned view of the manipulator shown in FIG. 8 along the section line A–C in FIG. 6 shows the other jaw or branch part 2, the groove provided in it and the groove block 6 passing through this groove.

According to FIGS. 7 and 8 the radii of curvature of the grooves and the groove blocks 8, 6 are different. With this the points of rotation indicated at R2b and R2a in FIG. 7 of the respective jaw or branch partss 2b and 2a lie closer to the longitudinal center axis of the instrument than the points of rotation R1, R2 of the jaw or branch parts 1 and 2 as are shown in FIG. 8.

The jaw or branch part 1 is thus pivotable about the point of rotation R1 and the jaw or branch part 2 about the point of rotation R2, whilst the jaw or branch part 2a is pivotable about the point of rotation R2a and the jaw or mouth part 2b about the point of rotation R2b.

In particular FIG. 9 representing the manipulator designed according to the invention in the open position shows that the jaw or branch parts 2a, 2b with respect to the resting instrument holder 13 are opened out or pivoted about a larger angle than the jaw or branch parts 1 and 2. This is due to the smaller radius of curvature of the groove blocks 7 and 8 guiding the jaw or branch parts 2a.

With the above described manipulator described in the FIGS. 6 to 9 the pivoting movement, i.e. the opening out and folding together of the jaw or branch parts is effected commonly by only one pull-push rod via four linkage arms linkedly connected to it and to the end of the jaw or branch part.

Variants of the instrument with more than two, i.e. e.g four or six jaw or branch parts may also be possible and furthermore such instruments are to be created with which in each case two branch parts associated together may be moved separately by a separate pull or push rod. Such separately movable jaw or branch parts may also as cited by way of FIGS. 6 to 9 have differing pivoting angles if correspondingly differing radii of curvature and arc lengths of the grooves and/or groove blocks guiding their pivoting movement are provided.

I claim:

1. A surgical instrument comprising:
   at least two distal jaw parts each having a proximal part;
   an instrument holder for enabling a user to hold the surgical instrument;
   a pull-push rod connected to said jaw parts for pivotably moving said jaw parts such that said jaw parts are movable commonly and in opposite directions from one another;
   a sliding block guide for guiding movement of said pull-push rod, comprising:
     a circular arc-shaped groove formed in said proximal part of each said jaw part, wherein each said circular groove in each respective jaw part is displaced by 180° from another said circular groove in another jaw part, each said circular groove defining a virtual circle;

at least two circular arc-shaped groove blocks disposed on said instrument holder, each said circular groove block being configured to slidably engage a corresponding said circular groove, such that a center of each said virtual circle is defined about each said groove block; and at least two linkage arms for enabling said pull-push rod to manipulate said jaw parts, each having a first end and a second end, said first end of each said linkage arm being connected to said push-pull rod, and said second end of each linkage rod being connected to said proximal part of said corresponding jaw part at a linkage point positioned at a predetermined distance from said virtual circle defined by said circular groove of said corresponding jaw part.

2. The surgical instrument of claim 1, further comprising a pair of through pins for commonly attaching said groove blocks to said instrument holder.

3. The surgical instrument of claim 2, wherein each said groove block is of a predefined arc length, and wherein a first portion of each said groove block distally of said through pins is of greater arc length than a second portion of each said groove block proximally of said through pins.

4. The surgical instrument of claim 1, wherein each said groove block is of a predefined width, smaller than a width of each said corresponding jaw part.

5. The surgical instrument of claim 1, comprising at least one additional jaw part, at least one additional corresponding groove block, and at least one additional corresponding linkage arm connected to said pull-push rod such that manipulation of said pull-push rod actuates all said connected jaw parts.

6. The surgical instrument of claim 1, comprising at least one additional jaw part, at least one additional corresponding groove block, at least one additional corresponding linkage arm and at least one additional pull-push rod connected to said additional jaw part, groove block and linkage arm, such that a portion of said jaw parts are capable of being actuated independently in a selective manner and in pairs by manipulation of at least one of said pull-push rod and said additional pull-push rod.

7. The surgical instrument of claim 6, wherein said groove blocks and said corresponding circular grooves are of a first predefined radii of curvature selected from a plurality of different curvature radii.

8. The surgical instrument of claim 7, wherein said additional groove blocks and said corresponding additional circular grooves defined on said additional jaw parts are of a second predefined radii of curvature selected from said plurality of different curvature radii.

9. The surgical instrument of claim 8, wherein said predetermined distance for said linkage points is different for at least a portion of linkage points for said additional jaw parts.

* * * * *